(12) United States Patent
Regensburger et al.

(10) Patent No.: US 12,740,686 B2
(45) Date of Patent: Sep. 22, 2026

(54) METHOD, COMPUTER PROGRAM, AND DATA PROCESSING UNIT FOR CREATING AT LEAST ONE CORRECTION VALUE FOR CORRECTING FLUORESCENCE INTENSITIES IN A FLUORESCENCE IMAGE, AND OPTICAL OBSERVATION SYSTEM

(71) Applicant: Carl Zeiss Meditec AG, Jena (DE)

(72) Inventors: Alois Regensburger, Oberkochen (DE); Christoph Hauger, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 194 days.

(21) Appl. No.: 18/238,444

(22) Filed: Aug. 25, 2023

(65) Prior Publication Data

US 2024/0065525 A1 Feb. 29, 2024

(30) Foreign Application Priority Data

Aug. 25, 2022 (DE) ..................... 10 2022 121 504.0
Aug. 25, 2022 (DE) ..................... 10 2022 121 505.9

(51) Int. Cl.
*G01N 21/64* (2006.01)
*A61B 1/00* (2006.01)
(Continued)

(52) U.S. Cl.
CPC ... *A61B 1/000095* (2022.02); *G01N 21/6428* (2013.01); *G01N 21/6458* (2013.01);
(Continued)

(58) Field of Classification Search
CPC ....... G01N 21/6458; G01N 2021/6439; G01N 21/274; G06T 2207/10064;
(Continued)

(56) References Cited

U.S. PATENT DOCUMENTS 6,392,794 B1 * 5/2002 Engelhardt ........ G02B 21/0032 359/368
9,182,347 B2 11/2015 Ishihara
(Continued)

FOREIGN PATENT DOCUMENTS

DE 19944148 A1 3/2001
DE 102005031104 A1 1/2007
(Continued)

OTHER PUBLICATIONS

Office Action issued in German Patent Application No. DE 10 2022 121 504.0, dated Apr. 6, 2023 (from which this application claims priority) and English language translation thereof.
(Continued)

*Primary Examiner* — Amandeep Saini
*Assistant Examiner* — Jaspreet Kaur
(74) *Attorney, Agent, or Firm* — Ewers IP Law PLLC; Falk Ewers

(57) ABSTRACT

A method for creating at least one correction value for correcting fluorescence intensities in a fluorescence image obtained with an optical observation system includes determining the parameter value of at least one parameter of the optical observation system which influences the observation of the fluorescence intensity, and generating the at least one correction value for correcting the fluorescence intensities in the fluorescence image based on the determined parameter value and the influence of the at least one parameter which influences the observation of the fluorescence intensity on the fluorescence intensities. A parameter of the illumination system serves as the at least one parameter which influences the observation of the fluorescence intensity. Additionally, a computer program, a computer-implemented method, a data processing unit, and an optical observation system for cre-
(Continued)

ating at least one correction value for correcting fluorescence intensities in a fluorescence image are provided.

18 Claims, 6 Drawing Sheets

(51) Int. Cl.
*G02B 21/00* (2006.01)
*G06T 5/50* (2006.01)

(52) U.S. Cl.
CPC ............ *G02B 21/0012* (2013.01); *G06T 5/50* (2013.01); *G01N 2021/6439* (2013.01); *G01N 2021/6478* (2013.01); *G01N 2201/129* (2013.01); *G06T 2207/10056* (2013.01); *G06T 2207/10064* (2013.01); *G06T 2207/10068* (2013.01); *G06T 2207/10152* (2013.01)

(58) Field of Classification Search
CPC . G06T 2207/10056; G06T 2207/10068; G06T 2207/1015; A61B 1/043
See application file for complete search history.

(56) References Cited

U.S. PATENT DOCUMENTS

| | | | | |
|---|---|---|---|---|
| 10,548,521 | B2 | 2/2020 | Schultz et al. | |
| 2002/0063863 | A1 | 5/2002 | Kask | |
| 2007/0014000 | A1* | 1/2007 | Nolte | G02B 21/361 359/368 |
| 2011/0152693 | A1 | 6/2011 | Schweitzer | |
| 2011/0313297 | A1 | 12/2011 | Ishihara | |
| 2012/0076434 | A1 | 3/2012 | Watanabe et al. | |
| 2013/0048875 | A1 | 2/2013 | Yamaguchi et al. | |
| 2014/0378843 | A1 | 12/2014 | Valdes et al. | |
| 2016/0116410 | A1 | 4/2016 | Blasinski et al. | |
| 2016/0278678 | A1 | 9/2016 | Valdes et al. | |
| 2019/0122345 | A1 | 4/2019 | Kamio et al. | |
| 2019/0227288 | A1* | 7/2019 | Themelis | A61B 1/00188 |
| 2022/0015857 | A1 | 1/2022 | DiCarlo et al. | |

FOREIGN PATENT DOCUMENTS

| | | | | |
|---|---|---|---|---|
| DE | 102006006014 | A1 | 9/2007 | |
| DE | 102008045886 | A1 | 3/2010 | |
| DE | 102011053777 | A1 | 3/2013 | |
| DE | 102014107445 | A1 * | 12/2015 | G02B 21/0012 |
| DE | 102014017006 | A1 | 5/2016 | |
| DE | 102017129519 | A1 | 6/2019 | |
| EP | 1528379 | A1 | 5/2005 | |
| JP | 2013089394 | A * | 5/2013 | |
| WO | 2006009906 | A2 | 1/2006 | |
| WO | 2006135769 | A1 | 12/2006 | |
| WO | 2007090591 | A1 | 8/2007 | |
| WO | 2015023990 | A1 | 2/2015 | |

OTHER PUBLICATIONS

Office Action issued in German Patent Application No. DE 10 2022 121 505.9, dated Aug. 2, 2023 (from which this application claims priority) and English language translation thereof.

Roberts et al, "Quantitative fluorescence in intracranial tumor: implications for ALA-induced PplX as an intraoperative biomarker", Journal of Neurosurgery, (Jul. 2011) ; 115(1): 11-17. doi: 10.3171/2011.2.JNS101451, Lebanon, New Hampshire.

* cited by examiner 100
10
1
4
14
16
18
24
6
10
2
5
40
10
42
A-A
10
12
8
3A
3B
3C
3D
3E
3F
3G
3H
3
TS

METHOD, COMPUTER PROGRAM, AND DATA PROCESSING UNIT FOR CREATING AT LEAST ONE CORRECTION VALUE FOR CORRECTING FLUORESCENCE INTENSITIES IN A FLUORESCENCE IMAGE, AND OPTICAL OBSERVATION SYSTEM

CROSS REFERENCE TO RELATED APPLICATIONS

This application claims priority to German patent applications DE 10 2022 121 504.0, filed Aug. 25, 2022, and DE 10 2022 121 505.9, filed Aug. 25, 2022, and the entire content of both applications is incorporated herein by reference.

TECHNICAL FIELD

The disclosure relates to a method, a computer program, and a data processing unit for creating at least one correction value for correcting fluorescence intensities in a fluorescence image. The disclosure further relates to an optical observation system suitable for carrying out the method.

BACKGROUND

Various fluorescence options enabling the observation of fluorescence can be integrated in modern optical observation systems which may include optical observation devices such as surgical microscopes and endoscopes for example. If the intention is to carry out a fluorescence measurement, then the latter is frequently based purely on the color impression and the perceived brightness under observation with the eye. However, this color impression and the brightness depend very strongly on very different parameters during the recording, and this does not allow for a reliable quantitative measurement. There therefore are recommendations to set the working distance and the illumination brightness to specific values in order to make fluorescence measurements better comparable.

For example, fluorescence recordings within the scope of neurosurgical operations depend on a plurality of parameters which influence the perceivable fluorescence intensity. In this context, it is frequently necessary to repeatedly modify parameters, for instance the working distance, the zoom setting, etc., during the neurosurgical operation. However, the observed or measured fluorescence intensity also changes with each modification. This leads to a tumor marked by a fluorescent dye shining brighter and darker at different times, depending on the current parameter set. However, since the luminosity of the fluorescence is included in the diagnosis for at least some fluorescence methods, comparability between a plurality of fluorescence measurements in different surgical situations, made by different users, and carried out in different clinics is sought after. In particular, quantitative fluorescence measurement methods are also sought after.

Quantitative measurements are possible with contact measurements at tissue points; however, such punctiform measurements made by handheld contact devices are not practical for the visualization of the fluorescence over a relatively large area or even live during the resection. By way of example, such contact measurements are described in "Quantitative fluorescence in intracranial tumor: implications for ALA-induced PpIX as an intraoperative biomarker", Roberts et al., Neurosurg. 2011 July; 115(1): 11-17. doi:10.3171/2011.2.JNS101451.

US 2019/227288 A1 describes a method for normalizing fluorescence intensities. In the method, parameter values of the observation beam path in an optical observation device, in particular the values for the settings of magnification and working distance, are acquired. The acquired parameter values and the influence of the corresponding parameters on the fluorescence intensity are used to set an exposure parameter for the image recording, in such a way that the influence of a modified magnification or a modified working distance on the recorded fluorescence intensities is compensated.

Fluorescence images are recorded in US 2016/278678 A1 and corrected based on a 3-D surface model. In particular, fluorescence images allowing a quantification of superficial and surface-near dyes are recorded. In the process, image deformations based on settings of the image recording and on the surface orientation of the observation object are determined and taken into account with a suitable image distortion.

Although quantitative fluorescence measurements are possible with the method described in US 2019/227288 A1 and US 2016/278678 A1, for example, there is the need to further reduce the influence on the fluorescence observation by the parameter values set for the setting parameters of the optical observation device.

SUMMARY

It is therefore an object of the disclosure to provide a method, a computer program, and a data processing unit for creating at least one correction value for correcting fluorescence intensities in a fluorescence image, and an optical observation system suitable for carrying out the method, with which the dependence of the observation of the fluorescence on the utilized observation parameters can be furthered reduced.

This object is achieved by a method for creating at least one correction value for correcting fluorescence intensities in a fluorescence image obtained with an optical observation system, a computer-implemented method for creating at least one correction value for correcting fluorescence intensities in a fluorescence image obtained with an optical observation system, a computer program for creating at least one correction value for correcting fluorescence intensities in a fluorescence image obtained with an optical observation system, a data processing unit for creating at least one correction value for correcting fluorescence intensities in a fluorescence image obtained with an optical observation system, and an optical observation system, as described herein.

According to a first aspect of the disclosure, a method for creating at least one correction value for correcting fluorescence intensities in a fluorescence image obtained with an optical observation system which includes an illumination system and an optical observation device is provided. In particular, the optical observation device can be an optical observation device in which the imaging is implemented with an imaging beam path. Examples of optical observation devices in which the imaging is implemented with an imaging beam path include endoscopes, cameras, or microscopes such as surgical microscopes. Optical observation devices in which the imaging is implemented with an imaging beam path should be distinguished from those optical observation devices in which imaging is implemented by virtue of scan points in the object being scanned and intensities recorded at scan points subsequently being combined to form an image. An imaging beam path is not present in that context. Examples of such optical observation devices include laser scanning microscopes or optical coherence tomography (OCT) systems. A surgical microscope differs from a laser scanning microscope in that (a) a surgical microscope has a working distance of 50 to 300 mm while a laser scanning microscope has a working distance of a few millimeters, e.g., up to 10 mm, and (b) in that a surgical microscope allows for a superimposition of fluorescence images and ordinary images taken with white light while a laser scanning microscope does not provide the possibility of such a superimposition."

The method includes the following steps:

determining the parameter value of at least one parameter of the optical observation system which influences the observation of the fluorescence intensity, and generating the at least one correction value for correcting the fluorescence intensities in the fluorescence image based on the determined parameter value and the influence of the at least one parameter which influences the observation of the fluorescence intensity on the fluorescence intensities.

In the method according to an aspect of the disclosure, a parameter of the illumination system finds use as the at least one parameter which influences the observation of the fluorescence intensity.

By way of example, the parameter value can be determined by acquiring the parameter value with a suitable sensor or by retrieving the parameter value from a controller. However, there is also the option of determining the parameter value by virtue of calculating the latter from at least one other acquired or retrieved parameter value based on a model.

The correction value can be a correction value for correcting the pixel values in the image or a correction value for correcting the parameter value of a setting parameter of the utilized optical observation system. The at least one correction value can accordingly be output to a unit with the correction value, for example an image processing unit or a setting unit, or be kept available for retrieval.

In the prior art, parameter values of the observation beam path of the optical observation device used for fluorescence observation, for instance the values for the settings of the magnification and the working distance, are taken into account and optionally corrected by adjusting parameter values. The prior art has also described the practice of taking account of the surface orientation of the observation object. This can reduce the influences of the observation parameters and the surface geometry on the observed fluorescence intensity. However, the observable fluorescence intensity depends not only on the observation parameters and the surface geometry but also on the level of the intensity of the excitation wavelength at the location of the fluorescence excitation. By taking account of the parameter value of at least one parameter of the illumination system, it is possible to improve the knowledge about the intensity of the excitation wavelength at the location of the fluorescence excitation, and it is possible to compensate fluctuations in the intensity of the excitation wavelength at the location of the fluorescence excitation which are based on settings in the illumination system. In combination with the consideration of the parameter values of setting parameters of the observation beam path and the consideration of the position and the orientation of the observation object, it is possible to take account of the essential influences on the fluorescence observation and optionally compensate these.

In particular, one of the following parameters can be used as the parameter of the illumination system: distance of an illumination system from the observation object, orientation of the illumination system in relation to the object regions, intensity of the illumination light source, spectral intensity distribution of the illumination light source, zoom setting of an illumination zoom, and position of an illumination stop.

The intensity of the excitation wavelength arriving at the observation object reduces with increasing distance between the illumination system and the observation object. Knowledge of the distance between the illumination system and the observation object therefore renders possible an accurate determination of the intensity of the excitation wavelength at the location of the fluorescence emission. The orientation of the observation object in relation to the illumination system likewise plays a role in relation to the intensity of the excitation wavelength at the location of the fluorescence emission. Depending on the orientation in relation to the illumination system, the illumination radiation is incident on an object region of the observation object in perpendicular fashion, or in skewed fashion to a greater or lesser extent. The more skewed the incidence of the illumination radiation, the lower the intensity of the illumination radiation available per unit area for the excitation of the fluorescence. Naturally, the intensity of the illumination light source, which is to say the intensity of the illumination radiation emitted by the illumination light source, also influences the intensity of the excitation wavelength available at the location of the fluorescence excitation. Likewise, the spectral intensity distribution of the illumination light source plays a role as it determines the level of intensity of a specific wavelength at a nominal brightness setting of the illumination system. A modification of the zoom setting of the illumination zoom leads to a reduction in the intensity of the excitation wavelength in the case of an increase in the zoom factor and to an increase in the intensity of the excitation wavelength in the case of a reduction of the zoom factor. The position of a possible illumination stop also co-determines the intensity of the excitation wavelength available at a location of the observation object. Thus, a stop might lead to vignetting, whereby the intensity of the excitation wavelength at the edge of the illumination light spot is lower than at the center of the illumination light spot. Influences of the illumination system can be removed from the fluorescence observation by calculation, or can be corrected therein, especially if all aforementioned parameters for generating the correction value are taken into account.

Typical illumination sources used to excite fluorescence, for instance xenon lamps and LEDs, are subject to aging effects which lead to a reduction in the intensity of the illumination light source over time. To take account of the aging effects, the current intensity of the illumination light source can be determined based on the value of a service life counter of the illumination source and the intensity nominally set for the illumination source, with use being made of a degradation model for the illumination source.

In addition to a reduction in the intensity of the illumination light source, shifts in the spectral intensity distribution of the illumination radiation also occur over time and lead to the degree by which the current intensity of the illumination light source has been reduced vis-à-vis the nominally set intensity depending on the wavelength of the illumination radiation. To be able to determine the current intensity of the excitation wavelength for the nominal intensity setting of the illumination light source as exactly as possible, it is therefore advantageous if use is made of a degradation model which takes account of not only the change in the overall intensity of the illumination source but also the shifts in the spectral intensity distribution of the illumination radiation that occur over time.

Instead of determining the aging effects based on the service life and the nominal intensity of the illumination light source, it is alternatively also possible to determine the current intensity of the illumination light source on the basis of a calibration target and the intensity of the reflected illumination light captured by the optical observation device when the calibration target is used. In a further alternative, there is the option of determining the current intensity of the illumination light source with the aid of an intensity sensor, with the intensity sensor typically being sensitive only or predominantly in the excitation range of the fluorescence. These two methods can be applied even if no service life counter is present and require no modification to the optical observation system or merely the attachment of an intensity sensor. In this context, the intensity sensor can be arranged at or in the optical observation system. Typically, it is arranged at or in the illumination system such that the intensity captured thereby does not depend on the parameter values of the observation beam path.

In an advantageous development of the method according to an aspect of the disclosure, there is a calculation of the fluorescence radiation emitted by at least one surface region of the observation object, with the spectral intensity distribution of the illumination light source being weighted in the calculation by the effective spectral excitation curve of the fluorescence. Based on such weighting, it is possible to take account of wavelength-dependent properties of the observation object when calculating the at least one correction value. In this way, it is possible to take account of the absorption of the excitation wavelength upon penetration into the observation object, for example.

In addition to the parameter value of the at least one parameter of the illumination system, it is possible to also determine and take account of the parameter value of at least one of the following parameters: distance of the optical observation device from the observation object, orientation of the optical observation device in relation to the observation object, zoom setting of the optical observation device, front focal distance of the optical observation device, stop setting of the optical observation device, gain of an image sensor used in the optical observation device, exposure duration of an image sensor used in the optical observation device, and nonlinearities of an image sensor used in the optical observation device.

All these parameters influence the observable intensity of the fluorescence. Taking these into account therefore significantly increases the field of application of the method according to an aspect of the disclosure.

In another advantageous development of the method according to an aspect of the disclosure, at least one reference measurement with a reference concentration of the fluorescent dye is carried out with a reference parameter value for the at least one parameter which influences the observation of the fluorescence intensity, in order to obtain a reference value for the fluorescence intensity at the reference concentration of the fluorescent dye. Then, a simulation of the expected fluorescence intensity is carried out, wherein a change in the fluorescence intensity in comparison with the reference intensity is determined for a deviation of the parameter value of the at least one parameter which influences the observation of the fluorescence intensity from the reference parameter value. Finally, a compensation factor is determined, with which it is possible to compensate a change in the fluorescence intensity in a digital image which is caused by the deviation of the parameter value of the at least one parameter which influences the observation of the fluorescence intensity from the reference parameter value.

The reference measurement and the compensation factor make it possible to depict surface regions with the same concentration of fluorescent dye with the same intensity of the fluorescence radiation in a digital image, independently of the distance and the orientation of a surface region in relation to the illumination system and in relation to the optical observation device.

Advantageously, the at least one reference measurement is carried out with reference parameter values for each parameter which influences the observation of the fluorescence intensity, and which is of relevance subsequently when observing a fluorescence intensity. The reference measurement supplies more accurate results in this way. By way of example, the reference measurement can be carried out on a reference observation object with a known surface geometry, in particular a plane surface, with the optical observation device and the illumination system each being in a reference position and a reference orientation in relation to the reference observation object. Within the scope of the described development, it is also possible to carry out a plurality of reference measurements with a plurality of mutually different reference concentrations, in order to obtain reference values for the fluorescence intensities assigned to the various reference concentrations. As a result, the reference intensity exhibiting the smallest deviation from the captured fluorescence intensity can be used in each case for the calculation of the compensation factors. As a result, the accuracy of the calculated compensation factors can be increased.

According to a second aspect of the disclosure, a computer-implemented method for creating at least one correction value for correcting fluorescence intensities in a fluorescence image obtained with an optical observation system which includes an illumination system and an optical observation device is provided. The computer-implemented method includes the following steps:

- receiving or retrieving the parameter value of at least one parameter of the optical observation system which influences the observation of the fluorescence intensity, and
- generating the at least one correction value for correcting the fluorescence intensities in the fluorescence image based on the received or retrieved parameter value and the influence of the at least one parameter which influences the observation of the fluorescence intensity on the fluorescence intensities.

In the computer-implemented method according to an aspect of the disclosure, a parameter of the illumination system finds use as the at least one parameter which influences the observation of the fluorescence intensity.

The at least one correction value can be output for use by another unit, for example an image processing unit or a setting unit, or can be kept available for retrieval.

According to a third aspect of the disclosure, a computer program for creating at least one correction value for correcting fluorescence intensities in a fluorescence image obtained with an optical observation system which includes an illumination system and an optical observation device is provided. The computer program includes instructions which, when executed on a computer, prompt the latter to:

- receive or retrieve the parameter value of at least one parameter of the optical observation system which influences the observation of the fluorescence intensity, and generate the at least one correction value for correcting the fluorescence intensities in the fluorescence image based on the received or retrieved parameter value and the influence of the at least one parameter which influences the observation of the fluorescence intensity on the fluorescence intensities.

In the computer program according to an aspect of the disclosure, a parameter of the illumination system finds use as the at least one parameter which influences the observation of the fluorescence intensity.

The computer program may moreover include instructions which, when executed on a computer, prompt the latter to output the at least one correction value for use by another unit, for example by an image processing unit or a setting unit, or to keep said at least one correction value available for retrieval.

According to a third aspect of the disclosure, a data processing unit for creating at least one correction value for correcting fluorescence intensities in a fluorescence image obtained with an optical observation system which includes an illumination system and an optical observation device is provided. The data processing unit includes a memory and a processor, with the processor, with a computer program stored in the memory, being configured to:

receive or retrieve the parameter value of at least one parameter of the optical observation system which influences the observation of the fluorescence intensity, and generate the at least one correction value for correcting the fluorescence intensities in the fluorescence image based on the received or retrieved parameter value and the influence of the at least one parameter which influences the observation of the fluorescence intensity on the fluorescence intensities.

In the data processing unit according to an aspect of the disclosure, a parameter of the illumination system finds use as the at least one parameter which influences the observation of the fluorescence intensity.

With the computer program stored in the memory, the data processing unit can moreover be configured to output the at least one correction value for use by another unit, for example by an image processing unit or a setting unit, or to keep said at least one correction value available for retrieval.

The advantages of the computer-implemented method according to an aspect of the disclosure, of the computer program according to an aspect of the disclosure, and of the data processing unit according to an aspect of the disclosure are evident from the method according to an aspect of the disclosure and are therefore not described in more detail here. Moreover, the computer-implemented method according to an aspect of the disclosure, the computer program according to an aspect of the disclosure, and the data processing unit according to an aspect of the disclosure can be developed such that they allow the implementation of the developments of the method according to an aspect of the disclosure.

According to a fifth aspect of the disclosure, an optical observation system having an illumination system and an optical observation device is provided. In particular, the optical observation device can be an optical observation device in which the imaging is implemented with an imaging beam path. Examples of optical observation devices in which the imaging is implemented with an imaging beam path include endoscopes, cameras, or microscopes such as surgical microscopes. Optical observation devices in which the imaging is implemented with an imaging beam path should be distinguished from those optical observation devices in which imaging is implemented by virtue of scan points in the object being scanned and intensities recorded at scan points subsequently being combined to form an image. An imaging beam path is not present in that context. Examples of such optical observation devices include laser scanning microscopes or optical coherence tomography (OCT) systems.

The optical observation system moreover includes a data processing unit according to an aspect of the disclosure. Moreover, it may include at least one of the following elements: a service life counter for registering the service life of the illumination source to date, an intensity sensor, an apparatus configured to determine the distance of the illumination system from the observation object and/or the orientation of the illumination system in relation to the observation object, an apparatus configured to determine the zoom position of an illumination zoom, and an apparatus configured to determine the position of an illumination stop.

The advantages of the optical observation system according to an aspect of the disclosure are evident from the method according to an aspect of the disclosure and are therefore not described in more detail here. The optical observation system according to an aspect of the disclosure can moreover be developed such that it allows the implementation of the developments of the method according to an aspect of the disclosure.

Moreover, it is advantageous for the optical observation system to include a controller which is configured to set at least one parameter value of the optical observation system in automated fashion, in order to ensure the use of an advantageously set parameter value.

BRIEF DESCRIPTION OF THE DRAWINGS

The disclosure will now be described with reference to the drawings wherein.

DESCRIPTION OF EXEMPLARY EMBODIMENTS

Figure 1:
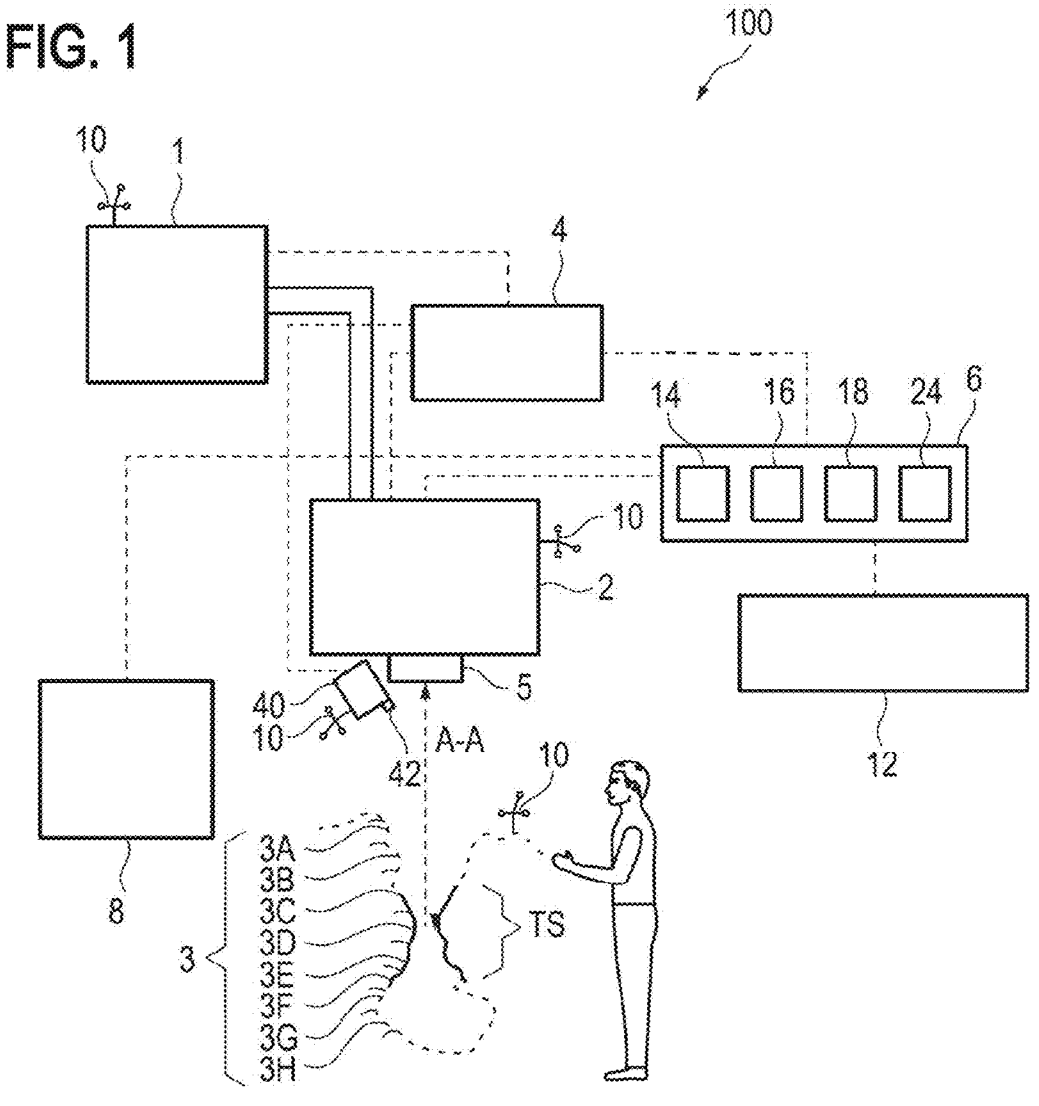
FIG. 1 shows an optical observation system for observing a fluorescence intensity of fluorescence radiation according to an exemplary embodiment of the disclosure.

FIG. 1 shows an optical observation system 100 according to an exemplary embodiment of the disclosure, in a very schematic illustration. In the present exemplary embodiment, the optical observation system 100 includes a surgical microscope 2 which is mounted on a stand 1, typically a robotic stand, and which serves as an optical observation device used to observe an observation object 3. The observation object 3 has an irregular structure with object regions 3A-H, which have different orientations and are at different depths. As a consequence, the object regions 3A-H have different distances from and orientations in relation to the surgical microscope 2. It should be observed here that the object regions are only depicted in a part of the observation object 3 in FIG. 1 for reasons of clarity.

The optical observation system 100 includes a controller 4 and a data processing unit 6 that prepares digital image data, recorded with an image sensor present in the surgical microscope 2, for display on a monitor 8, which may be a 3-D monitor in particular, and that outputs said data to the monitor 8. Further display units, for example a head-mounted display (HMD) or a digital eyepiece of the surgical microscope 2, may be present instead of the monitor 8 or in addition to the monitor, the data processing unit 6 transmitting to said further display units the digital image data prepared for display. In the present exemplary embodiment, loading a computer program can configure the data processing unit 6 to carry out a method for preparing the observation of a fluorescence intensity of fluorescence radiation of a fluorescent dye in the observation object 3. Alternatively, the data processing unit 6 may contain an application-specific integrated circuit (ASIC), in which the steps for carrying out the method are stored.

The optical observation system 100 moreover includes an illumination system 40, with which the observation object 3 can be illuminated with illumination light. In the present exemplary embodiment, the illumination system 40 can illuminate the observation object 3 with a specific wavelength, referred to hereinafter as excitation wavelength, which excites a fluorescent dye, introduced into the observation object 3, to emit fluorescence radiation. The surgical microscope 2 is configured to detect the fluorescence radiation emanating from the fluorescent dye. To this end, the surgical microscope 2 may include in particular a digital image sensor with a sufficient sensitivity to the wavelength of the fluorescence of the fluorescent dye. Moreover, at least one filter that is introducible into the observation beam path is present in the present exemplary embodiment and can be used to remove light at the excitation wavelength, which is reflected by the observation object 3, from the observation beam path. As a rule, the excitation is implemented at an intensity which would lead to the fluorescence radiation being swamped by the light at the excitation wavelength. This swamping can be prevented by the at least one filter that is introducible into the observation beam path.

Naturally, the fluorescence need not necessarily be observed by a display such as for example the monitor 8; instead, it may also be observed purely optically with eyepieces of the surgical microscope. Independently of whether the fluorescence is observed with eyepieces or with the aid of image sensors, the fluorescence intensity must exceed a certain minimum level in order to be able to be detected. In the case of an image sensor, the detection threshold in the corresponding wavelength range must be exceeded by the fluorescence intensity. However, a certain minimum intensity of the fluorescence radiation is required in the case of the visual observation as well, such that the eye as a detector can perceive the fluorescence radiation. The main field of use of the present disclosure, however, is the observation of fluorescence with the aid of digital image sensors such as charge-coupled device (CCD) sensors or complementary metal-oxide semiconductor (CMOS) sensors.

The optical components of a surgical microscope 2, which may find use as an optical observation device in the optical observation system 100, are explained hereinafter with reference to FIGS. 2 to 4. However, the disclosure may also be realized with other optical observation devices such as cameras or endoscopes, for example.

Figure 2:
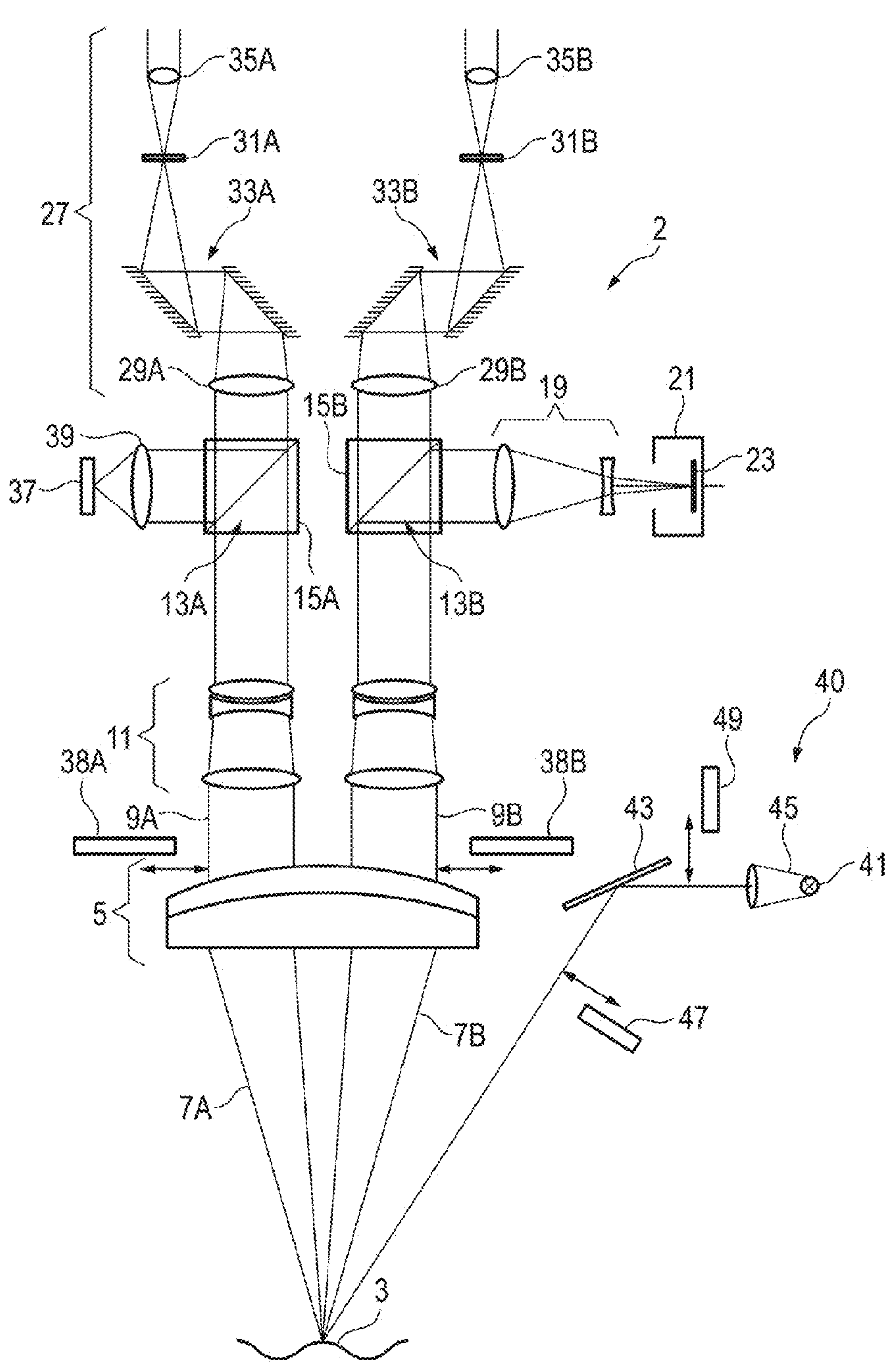
FIG. 2 shows the optical components of a surgical microscope as may find use as an optical observation device in the optical observation system, in a schematic illustration, FIG. 3 schematically shows the basic structure of a varioscope objective.

As essential optical constituent parts, the surgical microscope 2 shown in FIG. 2 includes an objective 5 which is intended to face an observation object 3 and which can be embodied as an achromatic or apochromatic objective in particular. In the present exemplary embodiment, the objective 5 has two partial lenses that are cemented to one another and form an achromatic objective. The observation object 3 is arranged in the focal plane of the objective 5 such that it is imaged at infinity by the objective 5. In other words, a divergent beam 7 emanating from the observation object 3 is converted into a parallel beam 9 during its passage through the objective 5. In this case, the image of the observation object is sufficiently focused in a depth range around the focal plane so as to be perceived in focus with the image sensor or the eye. Thus, this depth range is referred to as depth of focus and is denoted by reference sign “TS” in FIG. 1.

A magnification changer 11 is arranged on the observer side of the objective 5 and can be embodied either as a zoom system for changing the magnification factor in a continuously variable manner as in the illustrated exemplary embodiment, or as what is known as a Galilean changer for changing the magnification factor in a stepwise manner. In a zoom system, constructed by way of example from a lens combination having three lenses, the two object-side lenses can be displaced in order to vary the magnification factor. In actual fact, however, the zoom system also can have more than three lenses, for example four or more lenses, in which case the outer lenses then can also be arranged in a fixed manner. In a Galilean changer, by contrast, there are a plurality of fixed lens combinations which represent different magnification factors, and which can be introduced into the beam path in alternation. Both a zoom system and a Galilean changer convert an object-side parallel beam into an observer-side parallel beam with a different beam diameter. In the present exemplary embodiment, the magnification changer 11 already is part of the binocular beam path of the surgical microscope 2, which is to say it has a dedicated lens combination for each stereoscopic partial beam path 9A, 9B of the surgical microscope 2. In the present exemplary embodiment, a magnification factor is adjusted with the magnification changer 11 with a motor-driven actuator (not depicted here) which, together with the magnification changer 11, is part of a magnification changing unit for adjusting the magnification factor.

In the present exemplary embodiment, the magnification changer 11 is adjoined on the observer side by an interface arrangement 13A, 13B, with which external devices can be connected to the surgical microscope 1 and which includes beam splitter prisms 15A, 15B in the present exemplary embodiment. However, in principle, use can also be made of other types of beam splitters, for example partly transmissive mirrors. In the present exemplary embodiment, the interfaces 13A, 13B serve to output couple a beam from the beam path of the surgical microscope 2 (beam splitter prism 15B) and to input couple a beam into the beam path of the surgical microscope 2 (beam splitter prism 15A). However, they may both also be embodied to output couple a beam from the beam path of the surgical microscope 2 or both be embodied to input couple a beam into the beam path of the surgical microscope 2.

In the present exemplary embodiment, the beam splitter prism 15A in the partial beam path 9A serves to mirror information or data for an observer via the beam splitter prism 15A into the partial beam path 9A of the surgical microscope 2 with the aid of a display 37, for example a digital mirror device (DMD) or a liquid crystal display (LCD), and an associated optical unit 39. A camera adapter 19 with a camera 21 fastened thereto, said camera being equipped with an electronic image sensor 23, for example with a CCD sensor or a CMOS sensor, is arranged at the interface 13B in the other partial beam path 9B. It is possible with the camera 21 to record an electronic image and, in particular, a digital image of the observation object 3. The image sensor used can also be, in particular, a hyperspectral sensor comprising not just three spectral channels (e.g., red, green and blue), but rather a plurality of spectral channels. If both interfaces 13A, 13B are embodied to output couple a beam from the beam path of the surgical microscope 2, a camera adapter 19 with a camera 21 fastened thereto can be arranged on both interfaces 13A, 13B in each case. This allows spectroscopic images to be recorded.

Moreover, at least one further interface arrangement with at least two beam splitters may be present in the surgical microscope, wherein for example the one interface arrangement may serve to input couple stereoscopic partial images and the other interface arrangement may serve to output couple stereoscopic partial images.

The interface 13 is followed on the observer side by a binocular tube 27. The latter has two tube objectives 29A, 29B, which focus the respective parallel beam 9A, 9B onto an intermediate image plane 31, which is to say image the observation object 3 onto the respective intermediate image plane 31A, 31B. Finally, the intermediate images situated in the intermediate image planes 31A, 31B are imaged in turn at infinity by eyepiece lenses 35A, 35B, with the result that an observer can observe the intermediate image with a relaxed eye. Moreover, the distance between the two partial beams 9A, 9B is increased in the binocular tube with a mirror system or with prisms 33A, 33B in order to adapt said distance to the interocular distance of the observer. In addition, image erection is carried out by the mirror system or the prisms 33A, 33B.

The surgical microscope 2 moreover is equipped with an illumination system 40, with which the observation object 3 can be illuminated with illumination light. To this end, the illumination system 40 includes a white-light source 41, for instance a halogen lamp or a gas discharge lamp such as for example a xenon lamp, in the present example. However, light emitting diodes (LEDs) can also be considered for the light sources. The light emanating from the white-light source 41 is steered in the direction of the observation object 3 via a deflection mirror 43 or a deflection prism in order to illuminate said observation object. Furthermore, an illumination optical unit 45 is present in the illumination system 40 and ensures a uniform illumination of the entire observed observation object 3. Here, the illumination optical unit 45 may also include a zoom system (illumination zoom), which can modify the size of the illumination light spot, and/or a system which allows the focal distance of the illumination optical unit 45 to be varied. Moreover, the illumination system 40 may be equipped with a light source for emitting light at a wavelength which excites a fluorescence in a fluorescent dye that has been introduced into the observation object 3. Alternatively, as depicted in FIG. 2, a spectral filter 47 may be present; the latter can be introduced into the illumination beam path and substantially only allows passage of the wavelength of the light from the white-light source 41 which excites the fluorescence in the fluorescent dye. Moreover, filters 38A, 380B which block the wavelength exciting the fluorescence in the fluorescent dye are introduced into the observation beam path.

The illumination system 40 may moreover include at least one stop and/or at least one lens, with which it is possible to influence the profile of the illumination light cone emanating from the light source, for example in order to generate an illumination profile with emphasis on the center. The at least one stop and/or the at least one lens 49 can be introduced into the illumination beam path when necessary. Furthermore, the illumination system 40 may include stops that can bring about a sharp delimitation of the luminous field in the observation object 3.

Reference is made to the fact that the illumination beam path depicted in FIG. 2 is highly schematic and does not necessarily reproduce the actual course of the illumination beam path. In principle, the illumination beam path can be embodied as what is known as oblique illumination, which comes closest to the schematic illustration in FIG. 2. In the case of such oblique illumination, the beam path extends at a relatively large angle (6° or more) with respect to the optical axis of the main objective 5 and, as depicted in FIG. 2, may extend completely outside the main objective 5. Alternatively, however, there is also the possibility of allowing the illumination beam path of the oblique illumination to extend through a marginal region of the main objective 5. A further possibility for the arrangement of the illumination beam path is what is known as 0° illumination, in which the illumination beam path extends through the main objective 5 and is input coupled into the main objective 5 between the two partial beam paths 9A, 9B, along the optical axis of the main objective 5, in the direction of the observation object 3. Finally, it is also possible to design the illumination beam path as what is known as coaxial illumination, in which a first illumination partial beam path and a second illumination partial beam path are present. The illumination partial beam paths are input coupled into the surgical microscope 2 in a manner parallel to the optical axes of the observation partial beam paths 9A, 9B with one or more beam splitters, with the result that the illumination extends coaxially in relation to the two observation partial beam paths.

In the embodiment variant of the surgical microscope 2 shown in FIG. 2, the objective 5 only has an achromatic lens with a fixed focal length. However, use can also be made of an objective lens system made of a plurality of lenses, in particular a so-called varioscope objective, with which it is possible to vary the working distance of the surgical microscope 2, which is to say the distance between the object-side focal plane and the vertex of the first object-side lens surface of the objective 5, also referred to as front focal distance. The observation object 3 arranged in the focal plane is imaged at infinity by the varioscope objective 50, too, and so a parallel beam is present on the observer side.

Figure 3:
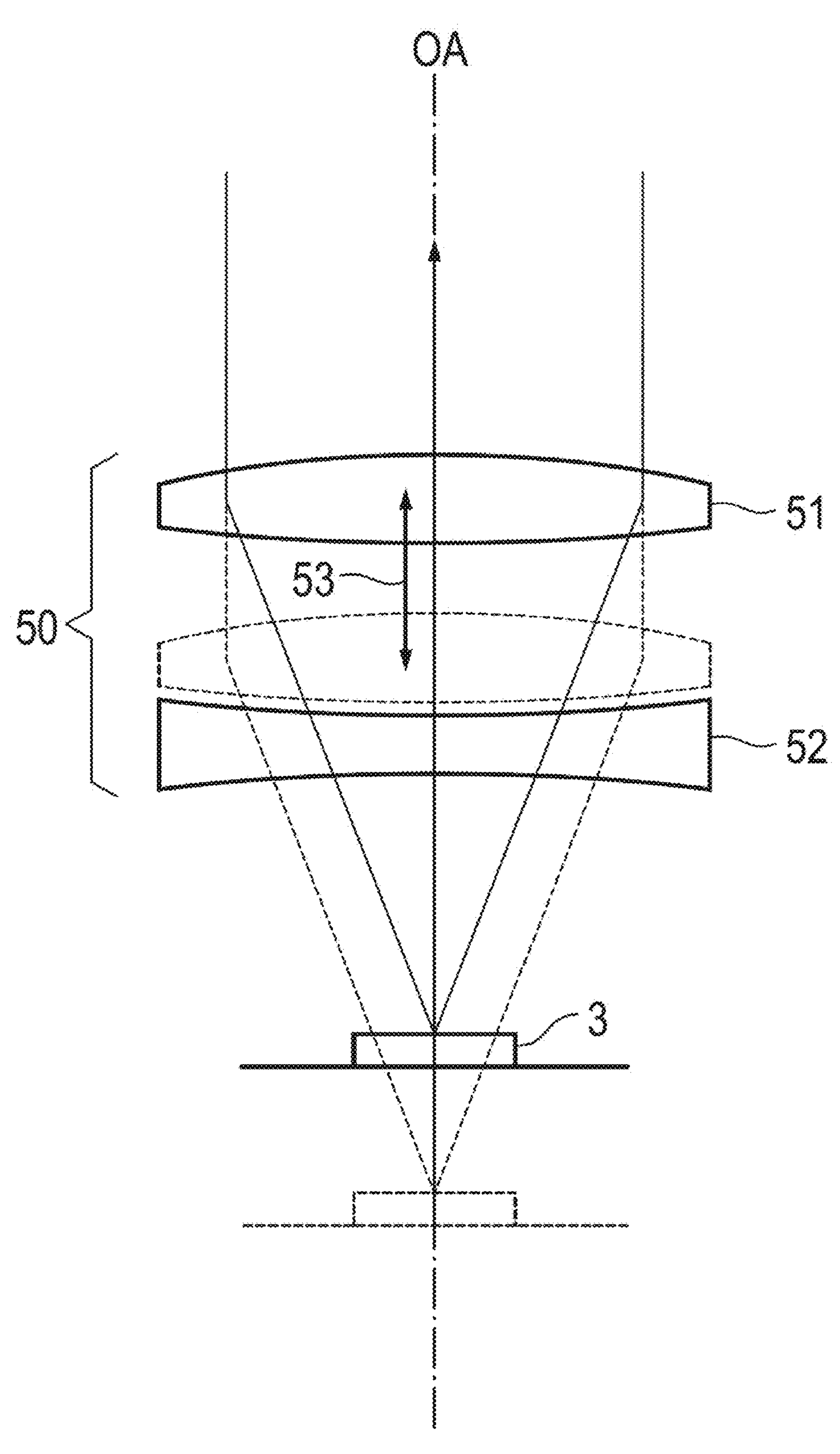

One example of a varioscope objective is depicted schematically in FIG. 3. The varioscope objective 50 includes a positive member 51, which is to say an optical element with positive refractive power, depicted schematically as a convex lens in FIG. 3. Moreover, the varioscope objective 50 includes a negative member 52, which is to say an optical element with negative refractive power, depicted schematically as a concave lens in FIG. 3. The negative member 52 is situated between the positive member 51 and the observation object 3. In the illustrated varioscope objective 50, the negative member 52 has a fixed arrangement, whereas, as indicated by the double-headed arrow 53, the positive member 51 is arranged to be displaceable along the optical axis OA. When the positive member 51 is displaced into the position illustrated by dashed lines in FIG. 3, the back focal length increases, and so there is a change in the working distance of the surgical microscope 2 from the observation object 3.

Even though the positive member 51 has a displaceable configuration in FIG. 3, it is also possible, in principle, to arrange the negative member 52 to be displaceable along the optical axis OA instead of the positive member 51. However, the negative member 52 often forms the last lens of the varioscope objective 50. A stationary negative member 52 therefore offers the advantage of making it easier to seal the interior of the surgical microscope 2 from external influences. Furthermore, it is noted that even though the positive member 51 and the negative member 52 in FIG. 3 are only illustrated as individual lenses, each of these members may also be realized in the form of a lens group or a cemented element instead of in the form of an individual lens, for example to embody the varioscope objective 50 to be achromatic or apochromatic.

Figure 4:
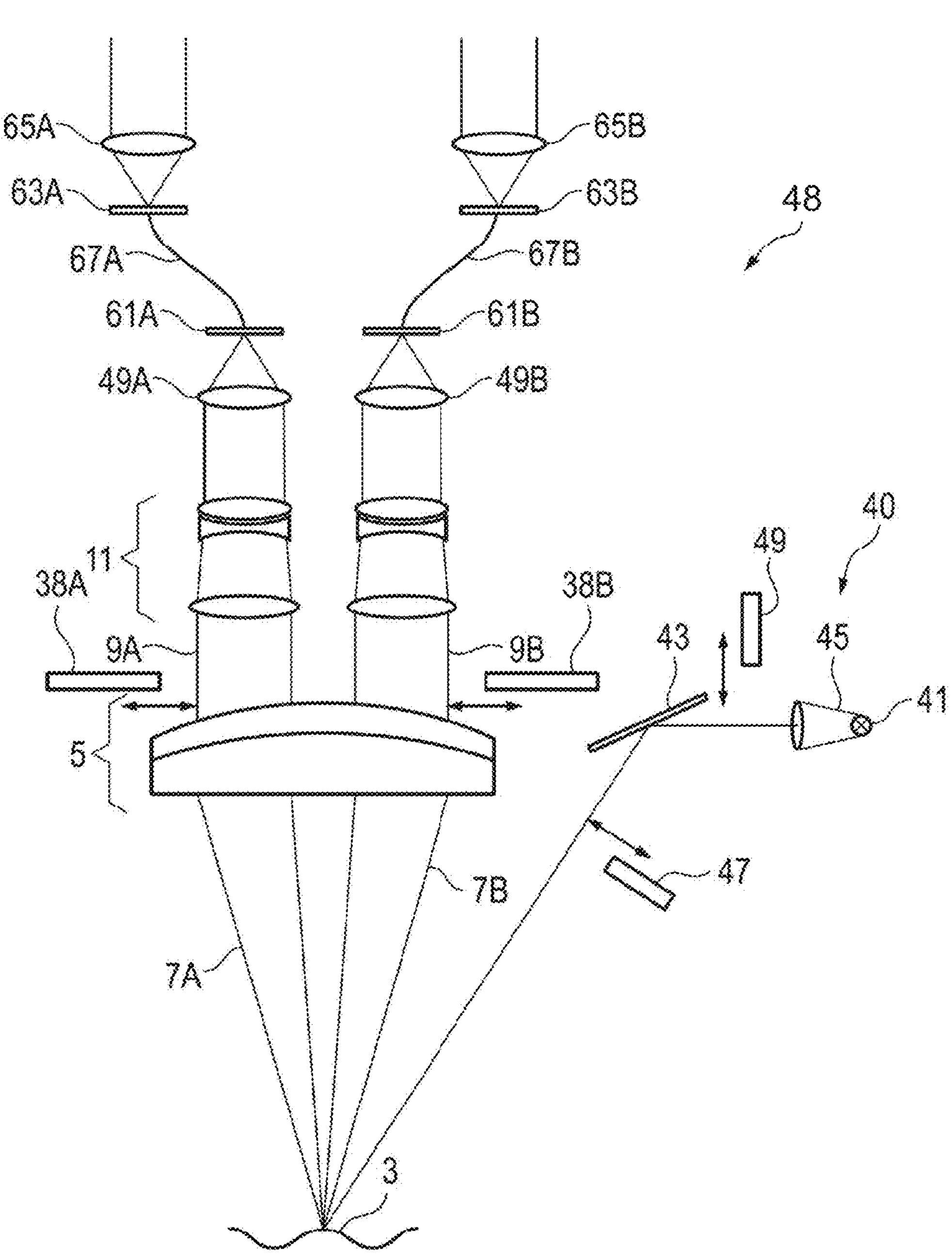
FIG. 4 shows the optical components of a digital surgical microscope as may find use as an optical observation device in the optical observation system, in a schematic illustration.

FIG. 4 shows a schematic illustration of an example of a purely digital surgical microscope 48. In this surgical microscope 48, the main objective 5, the magnification changer 11, and the illumination system 40 do not differ from the surgical microscope 2 depicted in FIG. 2. The difference lies in the fact that the surgical microscope 48 shown in FIG. 4 does not include an optical binocular tube. Instead of the tube objectives 29A, 29B from FIG. 2, the surgical microscope 48 depicted in FIG. 4 includes focusing lenses 49A, 49B which image the binocular observation beam paths 9A, 9B onto digital image sensors 61A, 61B. Here, the digital image sensors 61A, 61B can be CCD sensors or CMOS sensors, for example. The images recorded by the image sensors 61A, 61B are digitally transmitted to a data processing unit 6, as depicted in FIG. 1, which prepares said images for display on a monitor 8 or on digital displays 63A, 63B and then transmits said prepared images to the monitor 8 or the digital displays 63A, 63B. The digital displays 63A, 63B can be configured as LED displays, as LCD displays or as displays based on organic light-emitting diodes (OLEDs). Like in the present example, they can be assigned to eyepiece lenses 65A, 65B, with which the images displayed on the displays 63A, 63B are imaged at infinity such that an observer can observe said images with relaxed eyes. The displays 63A, 63B and the eyepiece lenses 65A, 65B can be part of a digital binocular tube; however, they can also be part of a head-mounted display (HMD) such as for instance a pair of smartglasses. In particular, the monitors or displays 63A, 63B can be designed for the observation of stereoscopic images. To this end, the displays 63A, 63B may be assigned to different eyes of the user and represent stereoscopic partial images. In the case of the monitor 8, the stereoscopic partial images can be depicted sequentially in time. With synchronized shutter glasses, for example, the stereoscopic partial images can then be displayed, exclusively in each case, to the appropriate eye. An alternative consists of depicting the stereoscopic partial images in differently polarized light and equipping the observer with a pair of glasses which, for the right and the left eye, in each case only allows polarized light from one of the stereoscopic partial images to pass.

Even though FIG. 4, like FIG. 2, depicts only one achromatic lens 5 with a fixed focal length, the surgical microscope 48 shown in FIG. 4 may include a varioscope objective instead of the objective lens 5, like the surgical microscope 2 illustrated in FIG. 3. Furthermore, FIG. 4 shows a transmission of the images recorded by the image sensors 61A, 61B to the displays 63A, 63B with cables 67A, 67B. Instead of in wired fashion, the images can also be transmitted wirelessly to the displays 63A, 63B, especially if the displays 63A, 63B are part of a head-mounted display.

In the exemplary embodiment shown in FIG. 1, the robotic stand 1, the surgical microscope 2, and the illumination system 40 each have a tracking target 10, with the aid of which a tracking system 12 can determine the position and orientation of the respective component. Moreover, a tracking target 12 is also attached directly or indirectly to the observation object 3, with the result that the position and orientation of the respective component can be determined in relation to the observation object 3. By way of example, the tracking target 12 may be fixed to a skull clamp for an indirect connection to the observation object 3.

Figure 5:
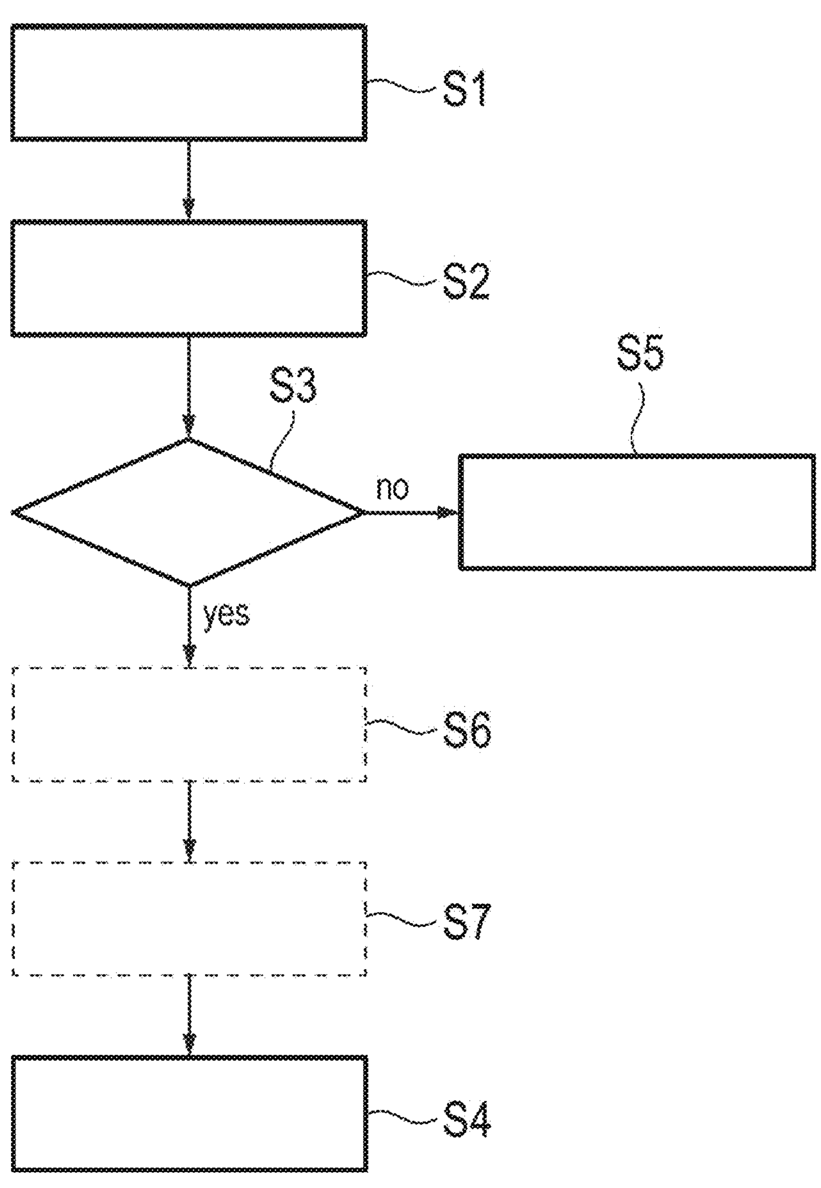
FIG. 5 shows a method for preparing the observation of a fluorescence intensity according to an exemplary embodiment of the disclosure.

A first exemplary embodiment of a method for preparing the observation of a fluorescence intensity with the optical observation system 100 depicted in FIG. 1 is described hereinafter with reference to FIG. 1 and FIG. 5, the latter showing a flowchart of the method.

The observation of fluorescence is important within the scope of tumor resection in particular, since the treating surgeon uses the fluorescence to assess which tissue is tumor tissue and therefore needs to be removed. However, this assumes that the fluorescence intensity of the tumor tissue is sufficient so as to be able to be detected throughout tumor tissue. However, some types of tumors, for example low-grade glioma (LLG), accumulate only very small amounts of contrast agent (e.g., PPIX in the case of low-grade glioma), with the result that the fluorescence intensity is very low and correspondingly difficult to measure. Even in the case of sensitive optical observation devices, the fluorescence intensity of PPIX in low-grade gliomas for example is often close to the detection threshold, and so optimal observation conditions must be ensured in order to be able to detect a reliable fluorescence signal with the image sensor 23 or the image sensors 61A, 61B. Thus, the prior art has seen cases where tissue regions located closer to the surgical microscope 2 (e.g., object regions 3A-C) appear to fluorescent since sufficient excitation light arrives at the tissue and enough of the emitted fluorescence is guided to the image sensor 23 or the image sensors 61A, 61B. However, tissue regions lower down (e.g., object regions 3D-H) in the same scene might no longer be illuminated sufficiently brightly with the excitation wavelength, despite having the same concentration of fluorescent dye, on account of the greater distance of the illumination light source 41, and/or the collection efficiency decreases on account of the greater distance of the surgical microscope 2 from the corresponding object regions 3D-H, for example with a (1/distance)^4 dependence overall. If the fluorescence intensity of the object regions 3A-C higher up is just above the sensitivity threshold of the image sensor 23 or image sensors 61A, 61B, then the same fluorescence intensity at tissue regions 3D-H lower down might just no longer be able to be detected by the image sensor 23 or image sensors 61A, 61B. That is to say, the situation may arise in which the image obtained by the image sensor 23 or image sensors 61A, 61B may contain some object regions 3A-C of the observation object 3 depicted in the image which can be illuminated and observed more efficiently and hence are depicted as a fluorescent, while other object regions 3D-H with the same concentration of fluorescent dye are depicted as non-fluorescent. This may lead to significant challenges for the treating surgeon, and these may unnecessarily lengthen the treatment. Additionally, the fluorescence may suddenly disappear or appear in the image obtained by the image sensor 23 or image sensors 61A, 61B following an adjustment to the surgical microscope 2 (e.g., change in zoom level, movement of the surgical microscope and/or of the illumination system 40 relative to the observation object 3), making a reliable diagnosis significantly more difficult.

The data processing unit 6 of the optical observation system 100 from FIG. 1 therefore includes a determination device 14 configured to determine the parameter value of at least one parameter which influences the observation of the fluorescence intensity. Moreover, it includes a simulation device 16 for simulating the fluorescence intensity expected for the respective object regions 3A-H based on the determined parameter values of a model for the influence of the at least one parameter on the fluorescence intensity. For each object region 3A-H, an evaluation device 18 of the data processing unit 6 then determines the expected fluorescence intensity for a given minimum concentration of the fluorescent dye. In the process, there can also be verification as to whether the determined fluorescence intensity is sufficient for detection by the image sensor 23 or image sensors 61A, 61B given the sensitivity thereof. If the evaluation device 18 determines that there are object regions 3A-H for which the minimum concentration of fluorescent dye does not lead to a signal that is detectable by the image sensor 23 or image sensors 61A, 61B, then the evaluation device 18 in the present exemplary embodiment outputs an alert which communicates to the user that a reliable detection of the fluorescence for the minimum concentration is not ensured.

Figure 6:
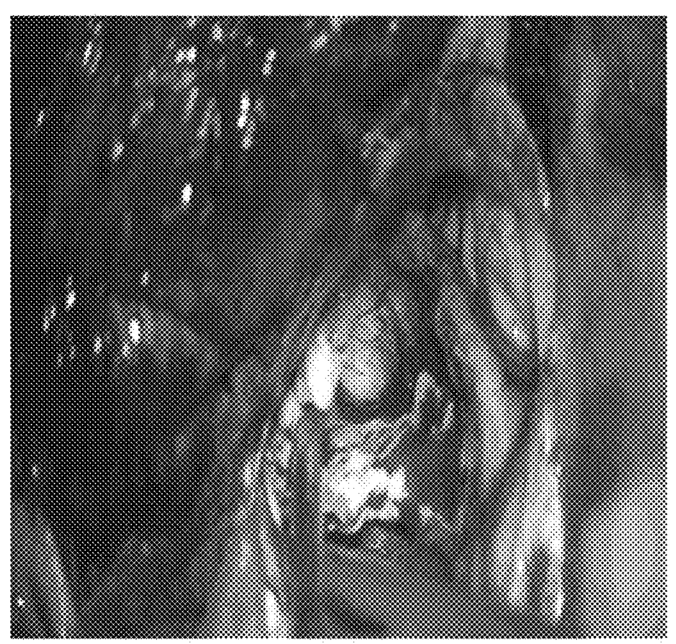
FIG. 6 shows an example of an observation object.
Figure 7:
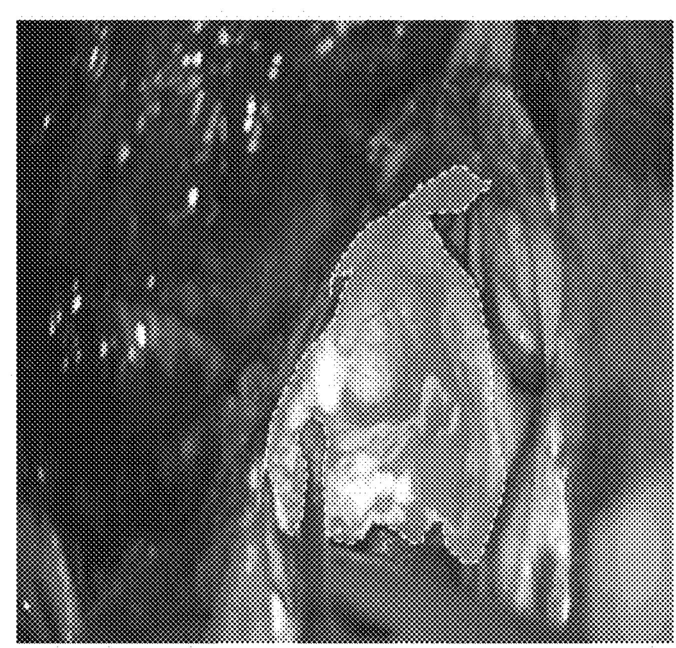
FIG. 7 shows the observation object from FIG. 6 with a marking indicating where the expected fluorescence intensity does not suffice to be able to be detected by the optical observation device given the sensitivity of the latter.

In an optional development, the evaluation device 18 can generate a graphical display, from which it is possible to read the object regions 3A-H in which the expected fluorescence intensity is not sufficient for detection by the image sensor 23 or image sensors 61A, 61B. In the simplest case, such a graphical display can be a contour line 20 which is superimposed on an image of the observation object 3, as shown in FIG. 6, and which surrounds those object regions in which the fluorescence intensity is insufficient for detection by the image sensor 23 or image sensors 61A, 61B (cf. FIG. 7). An alternative graphical display can be implemented in the form of a map. By way of example, object regions in which the minimum concentration of fluorescent dye leads to a detectable fluorescence intensity at the image sensor 23 or image sensors 61A, 61B may be colored differently in such a map than object regions for which the minimum concentration of fluorescent dye does not lead to a detectable fluorescence intensity at the image sensor 23 or image sensors 61A, 61B. Optionally, the map may have a color transition which specifies how "far away" the respective object regions still are from a reliable detection of the fluorescence intensity by the image sensor 23 or image sensors 61A, 61B. By way of example, object regions whose fluorescence intensity is only 10% below the fluorescence intensity required for detection by the image sensor 23 or image sensors 61A, 61B might be depicted in green while object regions at 50% below the required value of fluorescence intensity are colored red. The user can make a decision based on the graphical display as to whether the object regions in which the fluorescence intensity is not sufficient for detection by the image sensor 23 or image sensors 61A, 61B are relevant to the sought-after observation purpose, for instance a tumor resection. If the observed region of the observation object 3 is so large that it includes object regions known, for example from preliminary examinations, not to contain tumor tissue, then it may be acceptable in these regions for the minimum concentration of fluorescent dye not to lead to a fluorescence intensity detectable by the image sensor 23 or image sensors 61A, 61B.

Moreover, there is the option of the evaluation device 18 generating an improved parameter value for at least one parameter of the surgical microscope 2 and/or illumination system 40 and/or image sensor 23 or image sensors 61A, 61B by resorting to the simulation device 16, said improved parameter value leading to an increase in the number of object regions 3A-H in which the fluorescence intensity of the minimum concentration of fluorescent dye leads to a detectable signal at the image sensor 23 or image sensors 61A, 61B. The at least one improved parameter value can then either be set in automated fashion or be presented to the user as a settings recommendation, for example on the monitor 8.

In the present exemplary embodiment, the determination device 14, the simulation device 16, and the evaluation device 18 are integrated in the data processing unit 6 as software modules. However, they may also be integrated in the controller 4 of the optical observation system 100 or in a PC associated with the optical observation system 100. Further, there is the option of the determination device 14, the simulation device 16, and the evaluation device 18 to be integrated in different components of the optical observation system 100. By way of example, the determination device 14 may be integrated in the controller 4 and the simulation device 16 and the evaluation device 18 may be integrated in a PC. In principle, there is also the option of configuring the determination device 14 and/or the simulation device 16 and/or the evaluation device 18 as an independent hardware module.

In the present exemplary embodiment, the determination device 14, the simulation device 16, and the evaluation device 18 essentially carry out three steps. These are the acquisition of parameter values for parameters which influence the fluorescence intensity arriving at the image sensor (determination device 14 in step S1), the simulation of the fluorescence intensity arriving at the image sensor 23 or image sensors 61A, 61B from the respective object region 3A-H, with use being made of a model of the fluorescence observation which depends on the parameters for which the parameter values are acquired (simulation device 16 in step S2) in order to determine, for the individual object regions 3A-H, the expected fluorescence intensity at the location of the image sensor 23 or image sensors 61A, 61B for a given minimum concentration of the fluorescent dye, and the evaluation of the simulation (by the evaluation device 18 in step S3) in order to determine the object regions 3A-H at which the expected fluorescence intensity is sufficient for detection at the location of the image sensor 23 or image sensors 61A, 61B by the image sensor 23 or image sensors 61A, 61B for the given minimum concentration of the fluorescent dye. If the evaluation yields that there are object regions 3A-H present for which the minimum concentration of the fluorescent dye does not lead to a fluorescence intensity detectable by the image sensor 23 or image sensors 61A, 61B at the location thereof, then the evaluation device 18 can output an alert. Moreover, the evaluation device 18 can carry out further tasks, for example the creation of the above-described graphical display or the above-described generation of at least one improved parameter value.

The current parameter values of the parameters used in the simulation in step S2 are acquired in step S1. Examples of parameters which in the present exemplary embodiment may be included in the simulation include the distance of the surgical microscope 2 from the object regions 3A-H of the observation object 3, the orientation of the surgical microscope 2 in relation to the object regions 3A-H of the observation object 3, the zoom setting of the surgical microscope 2, the front focal distance of the surgical microscope 2, the stop setting of the surgical microscope 2, the gain of the image sensor 23 used in the surgical microscope 2 or of the image sensors 61A, 61B used in the surgical microscope, the exposure duration of the image sensor 23 used in the surgical microscope 2 or of the image sensors 61A, 61B used in the surgical microscope, nonlinearities of the image sensor 23 used in the surgical microscope 2 or of the image sensors 61A, 61B used in the surgical microscope, the distance of the illumination system 40 from the object regions 3A-H of the observation object 3, the orientation of the illumination system 40 in relation to the object regions 3A-H of the observation object 3, the intensity of an illumination light source 41, the spectral intensity distribution of an illumination light source 41, the zoom setting of an illumination zoom, and the position of an illumination stop.

To acquire the parameter values, the data processing unit 6 of the present exemplary embodiment includes a parameter value determination device 14, which retrieves the parameter values set at the surgical microscope 2, at the stand 1, and at the illumination system 40 from the controller 4. However, the parameter values may alternatively also be acquired by reading sensor measurement values. There is also the option of calculating parameter values indirectly from other parameter values that are acquired directly. By way of example, the relative position and the relative orientation of the surgical microscope 2 in relation to the observation object 3 can be calculated from the position and orientation of the surgical microscope 2, acquired in the coordinate system of the tracking system 12 with the tracking system 12, and the position and orientation of the observation object, likewise acquired in the coordinate system of the tracking system 12 with the tracking system 12. Alternatively, the positions and the orientation of the surgical microscope 2 in relation to the object regions 3A-H of the observation object 3 can be determined with stereographic methods from stereoscopic images of the observation object. Variables such as the zoom setting of the surgical microscope 2 or of the illumination system 40 can be read by the determination device 14 directly from the controller 4 of the surgical microscope 2 and of the illumination system, like in the present exemplary embodiment, or can be acquired by sensors in the respective zoom system. The intensity and the spectral intensity distribution of the illumination light source 41 can also be acquired indirectly by virtue of being calculated based on characteristics from the values of a service life counter, which registers the service life of the illumination light source to date.

On account of a degradation of the illumination light source 41 over time, the intensity of the excitation wavelength currently output by the illumination light source 41 deviates from the nominally set intensity of the excitation wavelength over time. The nominally set intensity of the excitation wavelength in this case emerges from the nominally set intensity of the illumination light source 41 and the spectral intensity distribution thereof. In the present exemplary embodiment, the intensity of the excitation wavelength currently output by the illumination light source 41 can be determined with an intensity sensor 42 which is installed in the surgical microscope 2 or in the illumination system 40. The intensity sensor 42 is typically sensitive exclusively, or at least predominantly, to the excitation wavelength in order to obtain the most accurate acquisition possible of the intensity of the excitation wavelength for the fluorescence. Optionally, the spectral intensity distribution of the illumination light can also be determined with an intensity sensor, for instance with the aid of a multispectral sensor. The intensity currently output by the illumination light source 41 at the excitation wavelength (or the spectral intensity distribution of the illumination light) given the nominally set intensity of said illumination light source may however alternatively or additionally also be determined by virtue of a calibration target (e.g., a white sheet of paper), placed under the surgical microscope 2 and focused prior to the actual observation, being recorded by the image sensor 23 or image sensors 61A, 61B and the signal generated in the image sensor 23 or image sensors 61A, 61B in the process being evaluated. Typically, only the color channel/channels of the image sensor or sensors that comes/come closest to the excitation wavelength is/are evaluated. The determined intensity can then be used in the simulation in step S2. However, the deviation of the current intensity of the excitation wavelength from the intensity of the excitation wavelength arising from the nominally set intensity of the illumination light source 41 may optionally also be determined from the determined intensity of the excitation wavelength and a correction value can be generated, with the setting of the illumination light source 41 having to be corrected by said correction value in order to obtain a current intensity of the excitation wavelength which corresponds to the nominal intensity of the excitation wavelength. Thus, the intensity of the illumination light source 41 can be adapted in such a way with the correction value that the degradation of the illumination light source 41 is just compensated for within the scope of the fluorescence excitation.

A further alternative or additional option configured to determine the intensity of the excitation wavelength currently given off by the illumination light source 41 having the nominally set intensity lies in the determination thereof via a service life counter of the illumination light source 41 (typically a xenon lamp or LED) and the normally set intensity for the illumination light source 41. As the service life of the illumination light source increases, the intensity of the illumination light emitted thereby decreases, with the result that its actual intensity deviates from the nominally set intensity. The current intensity of the illumination light source 41 can be determined from the nominally set intensity based on the service life of the illumination source 41 to date and can be used in the simulation in step S2. Optionally, it is possible here, too, to generate a correction value from the degree by which the current intensity of the illumination light source 41 has been reduced vis-à-vis the nominally set intensity, said correction value specifying the amount by which the intensity of the illumination light source 41 must be corrected in order to obtain a current intensity that corresponds to the nominally set intensity. Thus, the intensity of the illumination light source 41 can be adapted in such a way with the correction value that the degradation of the illumination light source 41 is just compensated for within the scope of the fluorescence excitation. In addition to the change in the overall intensity of the illumination source 41, the utilized degradation model for the illumination light source 41 may optionally also take account of the shifts in the spectral intensity distribution of the illumination radiation that occur over time. The shift in the spectral intensity distribution leads to the degree by which the current intensity of the illumination light source 41 is reduced vis-à-vis the nominally set intensity being dependent on the wavelength. The current intensity can be determined for each wavelength of the illumination light by taking account of the shifts in the spectral intensity distribution that occur over time. By taking account of the shifts in the spectral intensity distribution that occur over time, it is moreover possible to generate a correction value matched precisely to the excitation wavelength of the fluorescence.

Based on the corrected excitation wavelength, it is possible to perform a calculation as to how much fluorescence radiation is emitted. In the calculation process, the spectral intensity distribution of the illumination light source 41 can be weighted by the effective spectral excitation curve of the fluorescence. Based on such weighting, it is possible within the scope of the calculation of the at least one correction value to take account of the wavelength-dependent properties of the observation object 3, for example the absorption of the excitation wavelength upon penetration into the observation object.

The optional correction of the setting of the illumination light source 41 can be implemented in automated fashion, with the result that the actual intensity of the illumination light source always corresponds to the nominally set intensity. However, there is also the option of communicating to the user the manner in which the setting of the illumination light source 41 needs to be adapted in order to obtain a desired intensity of the illumination light source.

In step S2, there then is a simulation of the fluorescence emission based on a model for the observation of the fluorescence intensity, with a concentration of fluorescent dye corresponding to a given minimum concentration being assumed for the simulation. The model includes parameters of the illumination system 40, parameters of the surgical microscope 2, and parameters of the image sensor 23 or image sensors 61A, 61B, which parameters are considered in detail hereinafter. In the present exemplary embodiment, the simulation is carried out by a simulation device 16 that is integrated in the data processing unit 6.

The parameters of the illumination system 40 determine, inter alia, the emission intensity of the illumination light source 41 and the emission wavelength of the illumination light source 41, and hence the excitation wavelength. Moreover, the distance of the illumination system 40 from the object regions 3A-H of the observation object 3 and the orientation of the illumination system 40 in relation to the object regions 3A-H of the observation object 3, the zoom setting of the illumination system 40, and the position of stops in the illumination system 40 determine the amount of excitation radiation reaching an object region 3A-H per unit area. This influences the intensity of the excitation wavelength at the location of the fluorescence excitation and hence also the intensity of the fluorescence emission, whereby in turn the fluorescence intensity arriving at the pixels of the image sensor 23 or image sensors 61A, 61B is influenced.

The parameters of the surgical microscope 2 determine how much fluorescence radiation emitted by an object region 3A-H of the observation object 3 reaches the image sensor 23 or image sensors 61A, 61B (or the eyepiece). In this case, the distance of the surgical microscope 2 from the object regions 3A-H of the observation object 3 and the orientation of the surgical microscope 2 in relation to the object regions 3A-H of the observation object 3, the zoom setting in the surgical microscope 2, and the transmission behavior of stops (vignetting) and filters (transmittance) introduced into the observation beam path are of particular importance to the fluorescence intensity that reaches the image sensor 23 or image sensors 61A, 61B, and hence to the signal strength caused in the pixels of the image sensor 23 or image sensors 61A, 61B.

In an image sensor, the gain (amplification factor), the exposure duration, nonlinearities of the image sensor, and other variable factors of the image sensor influence the signal strength caused in the pixels of the image sensor by the incident fluorescence intensity.

Within the scope of the simulation in step S2, an optics and system model is typically used to take account of the influence of all the aforementioned parameters when calculating the signal strength caused in the pixels of the image sensor 23 or image sensors 61A, 61B when the minimum concentration of fluorescent dye is present.

An example of a possible optics and system model is as follows:

Sensor signal=(1/illumination term)*(1/collection term)*(1/sensor term)*raw signal In this case, the illumination term arises from the parameter values of the illumination system 40, the collection term arises from the parameter values of the surgical microscope 2, and the sensor term arises from the parameter values of the image sensor 23 or image sensors 61A, 61B.

A possible illumination term is as follows:

Illumination term=[(zoom factor illumination)^2*(linear stop-down factor illuminance)/(illumination to object surface distance)^2]*luminous_intensity_factor_with_spectral_excitation_weight*cos (angle between illumination and surface of the observation object)

A possible collection term is as follows:

Collection term=collection efficiency(zoom factor, focusing)/(objective to surface of the observation object distance)*directional_characteristic_function_of_the_fluorescence_emission (angle of observation with respect to the surface of the observation object)*image_location_dependent_vignetting_factor A possible sensor term is as follows:

Camera term=camera_response_function(exposure time, gain, measured raw signal)

Typically, shading effects by the observation object 3 are also included when calculating the illumination term and the collection term. For example, this can be implemented with the aid of a stereographically obtained 3-D depth map. Rather than with stereography, the 3-D depth map may also be generated with any other method known per se, for example with a depth sensor, with structured illumination, etc.

The illumination term, the collection term, and the raw signal are calculated for a respective pixel of the image sensor 23 or image sensors 61A, 61B and the object region 3A-H of the observation object 3 imaged thereon. Thus, in the present exemplary embodiment, the size of an object region 3A-H of the observation object 3 arises from the imaging factor used to image the observation object 3 onto the image sensor 23 or image sensors 61A, 61B, the imaging factor depending inter alia on parameters of the surgical microscope 2, for example on the zoom setting, the working distance, etc. Moreover, the size of the object regions 3A-H which are imaged on a pixel of the image sensor 23 or image sensors 61A, 61B can be increased by virtue of combining a plurality of adjacently arranged pixels to form a larger pixel (known as binning), in order to increase the effective pixel area.

Subsequently, in step S3, the evaluation device 18 evaluates the result of the simulation from step S2 to the effect of whether there are object regions 3A-H present, for which the fluorescence intensity, as determined for the given minimum concentration of the fluorescent dye, is not sufficient for detection by the image sensor 23 or image sensors 61A, 61B at the location of the image sensor 23 or image sensors 61A, 61B. If the evaluation yields that there are object regions 3A-H present for which the minimum concentration of the fluorescent dye does not lead at the location of the image sensor 23 or image sensors 61A, 61B to a fluorescence intensity detectable thereby, then the evaluation device 18 outputs an alert in the present exemplary embodiment (step S4). The alert can optionally be accompanied by a graphical display which indicates the object regions which at the location of the image sensor 23 or image sensors 61A, 61B do not lead to a fluorescence intensity detectable by the image sensor 23 or image sensors 61A, 61B, so that the user can estimate the relevance of the alert. If the evaluation yields that there are no object regions which at the location of the image sensor 23 or image sensors 61A, 61B do not lead to a fluorescence intensity detectable by the image sensor 23 or image sensors 61A, 61B, then the preparation of the fluorescence observation is complete, and the fluorescence observation can be performed (step S5).

Optionally, the evaluation device 18 can moreover carry out further tasks. By way of example, it may carry out the aforementioned generation of at least one improved parameter value. The optional generation of the at least one improved parameter value is implemented in step S6 either in automated fashion or following a request by the user should the evaluation in step S3 yield that there are object regions 3A-H present which, for the minimum concentration of the fluorescent dye, do not lead at the location of the image sensor 23 or image sensors 61A, 61B to a fluorescence intensity that is detectable by said sensor/sensors. Then, in step S6, the evaluation device 18 generates an improved parameter value for at least one parameter which influences the fluorescence intensity at the location of the image sensor 23 or image sensors 61A, 61B, said parameter value leading to a reduction in the number of object regions 3A-H for which the minimum concentration of the fluorescent dye does not lead to a fluorescence intensity that is detectable by the image sensor 23 or image sensors 61A, 61B at the location of said image sensor or image sensors. To improve the parameter value, the evaluation device 18 can for example vary the corresponding parameter value and calculate a quality value for each value of the parameter occurring during the variation. By way of example, the number of object regions for which the minimum concentration of the fluorescent dye does not lead to a detectable fluorescence intensity at the location of the image sensor 23 or image sensors 61A, 61B can be used as a quality value in this context. Optionally, there can also be weighting in the process as regards to where in the image the remaining object regions for which the minimum concentration of the fluorescent dye does not lead to a detectable fluorescence intensity at the location of the image sensor 23 or image sensors 61A, 61B are located. By way of example, object regions in the center of the image may experience a higher weight than object regions at the edge of the image. Then, the at least one parameter can be improved until the quality value reaches a minimum or drops below a specified value. Alternatively, the number of regions for which the minimum concentration of the fluorescent dye leads to a detectable fluorescence intensity at the location of the image sensor 23 or image sensors 61A, 61B can be used as a quality value. Then, the at least one parameter can be improved until the quality value reaches a maximum or drops below a minimum value. In this case, too, there can be a different weight for object regions in the center of the image vis-à-vis object regions at the edge of the image field. The improved parameter value of the at least one parameter then can either be set in automated fashion (step S7) or be displayed for the user as a recommended setting. By way of example, at least one of the following improvements can be implemented:

alignment of the viewing angle of the surgical microscope 2 and/or illumination system 40 via the stand 1, optimization of the luminous intensity of the optical unit of the surgical microscope 2 (zoom setting, working distance), optimization of the sensitivity of the image sensor 23 or image sensors 61A, 61B, and increase in the illumination brightness.

Within the scope of the method, the user can also be offered the option of setting, for example in the controller 4 or evaluation device 18, which parameters which influence the observation of the fluorescence intensity should be improved automatically by the evaluation device 18 and which they would like to improve manually themselves.

If the concentration of fluorescent dye in the vicinity of the surface should be determined in the fluorescence observation that is carried out following the preparation of the fluorescence observation, then the signal detected by the image sensor 23 or image sensors 61A, 61B must be corrected on the basis of a pre-factor.

Corrected signal=pre-factor*(1/illumination term)*(1/collection term)*(1/sensor term)*raw signal To this end, the pre-factor introduced into the optics and system model can be determined for each fluorescent dye and for an assumed tissue type by calibration. Typically, a different pre-factor is used depending on the tissue type. If it is only the fluorescence intensity to be expected with the minimum concentration that should be determined for each object region, then it is possible to determine a suitable pre-factor based on a model of the emission procedure and the properties of the employed optical system.

Reference objects are used for the calibration. For example, a first reference object is a diffusely reflecting white object, which diffusely reflects 50% of the radiated-in light intensity. By way of example, a second reference object is an aqueous solution in a reference vessel, containing a reference concentration of 100 nM of the fluorescent dye. Moreover, reference poses and orientations of the surgical microscope 2 and the illumination system 40 are defined in relation to the respective reference object. A respective reference parameter value is defined for all parameters of the surgical microscope 2, of the illumination system 40, and of the image sensor 23 or image sensors 61A, 61B that are included in the simulation.

By way of example, the reference parameter values may (but need not) be chosen such that the following reference conditions are present during the calibration:

a perpendicular observation of the surface of the reference object (reference observation angle 90°), a reference location within the image on the image sensor: the object is situated in the centre of the image and imaged on the central pixel, a reference working distance of 200 mm between the surgical microscope 2 and the object, a reference position of the surgical microscope 2 (reference focal position=200 mm, reference zoom factor of the observation optical unit gamma_observation=1, reference stop position: stop 100% open), a reference brightness of the illumination of 50%: reference age of the lamp: new xenon lamp, a reference setting of the illumination stop (completely open) and illumination zoom (mid position of the illumination zoom, zoom factor gamma illumination=1), and a reference setting of the image sensor parameters: gain=0, exposure time 20 ms, etc.

The calibration under the reference conditions leads to the determination of the signal at the image sensor 23 or image sensors 61A, 61B (i.e., the central reference pixel of the image sensor in the present example) which is generated by the light reflected by the first reference object if the illumination of the first reference object is implemented at the reference brightness and the remaining reference settings are present. By way of example, the first reference object generates a raw reference signal of 100 HE (brightness units) on the reference pixel of the image sensor 23 or image sensors 61A, 61B as a result of reflecting the illumination light under the aforementioned reference conditions. Thus, for the case of the reference conditions being present, a reference intensity in the form of a reference signal of likewise 100 HE is stored in the data processing unit.

Moreover, the calibration under the reference conditions leads to the determination of the signal at the image sensor 23 or image sensors 61A, 61B (i.e., the central reference pixel of the image sensor in the present example) which is present if the fluorescence is implemented in the second reference object with the reference intensity of the excitation wavelength. By way of example, the second reference object generates a raw reference signal of 100 HE (brightness units) on the reference pixel of the image sensor 23 or image sensors 61A, 61B as a result of a fluorescence emission excited by the excitation wavelength under reference conditions. Thus, for the case of the reference conditions being present, a reference intensity in the form of a reference signal of likewise 100 HE is likewise stored in the data processing unit 6.

An object of the calibration is to ensure that, independently of whether the actual parameters values deviate from the reference parameter values, the same signal of 100 HE is always detected by the optical observation system 100 according to an aspect of the disclosure when the reference object is observed. It is a further object of the calibration that there is a linear relationship between the diffuse reflectivity of an observation object 3 and the acquired signal, or between the fluorescent dye concentration of the observation object 3 and the acquired signal. By way of example, in the case of a fluorescence observation with a concentration of fluorescent dye of 10 nM, 50 nM, 70 nM, etc., which deviates from the reference concentration of 100 nM, a corrected signal of 10 HE, 50 HE, 70 HE, etc., should be detected in the case of an otherwise identical second reference object. For the case of an observation of reflected light (e.g., white-light observation), for example, a first reference object with a diffuse reflectivity of 10%, 20%, 30%, etc., which deviates from the reference reflectivity of 50%, should always be detected with a corrected signal of 10 HE, 20 HE, 30 HE, etc.

To ensure this, the data processing unit 6 of the present exemplary embodiment stores, in the memory of the signal processing unit 24 with calibration or calculation in advance and for each parameter which influences the observation of the fluorescence intensity, a relationship between the deviation of the actual value of the respective parameter from its reference value and the deviation of the signal at the image sensor 23 or image sensors 61A, 61B which represents the measured intensity from the reference signal which represents the reference intensity. By way of example, a data processing unit 6 may store the fact that an actual zoom factor gamma_observation=2, which deviates from the reference zoom factor gamma_observation=1 of the observation optical unit, leads to a reduction in the signal, and hence in the measured intensity, by a factor of 0.25. By way of example, the relationship can be stored as an equation or a system of equations. Alternatively, it may be stored in the form of a value table or a plurality of value tables. It is also possible that the relationship is stored as an equation or system of equations for some parameters and stored in the form of a value table or a plurality of value tables for other parameters. Interpolations or extrapolations can also be carried out between the stored values in the case of one or more value tables.

With the aid of the formula or formulas stored in the data processing unit 6 or with the aid of the value table or value tables stored in the data processing unit 6, it is possible to convert a measured intensity, in particular a measured fluorescence intensity, into a corrected intensity, in particular a corrected fluorescence intensity. By way of example, if only the actual zoom factor gamma_observation=2 deviates from the reference zoom factor gamma_observation=1 in the case of actual conditions of the observation which otherwise correspond to the reference conditions, then the image sensor 23 or image sensors 61A, 61B capture a measured raw signal of 25 HE for the reference concentration of fluorescent dye. Thus, to correct the raw signal, the raw signal is divided by a deviation factor of 0.25 in order to obtain a corrected signal of 100 HE, which corresponds to the fluorescence intensity of the reference concentration of the fluorescent dye of 100 nM.

In another example, the raw signal has been reduced for example by a deviation factor of 0.2 on account of vignetting of the optical unit at the edge of the image sensor 23 or image sensors 61A, 61B, in the case of otherwise unchanged reference conditions. To correct the raw signal, the latter is divided by the deviation factor of 0.2 for pixels at the edge of the image sensor 23 or image sensors 61A, 61B, with the result that a corrected signal of 100 HE arises in turn.

In yet another example, the raw signal has been increased by a factor of 9 to a raw signal of 900 HE in the case of an illumination zoom factor gamma illumination=3 and otherwise unchanged reference conditions. Thus, to correct the raw signal, the raw signal of 900 HE is divided by a deviation factor of 9 in order to obtain a corrected signal of 100 HE, which corresponds to the fluorescence intensity of the reference concentration of the fluorescent dye of 100 nM.

Various parameters which influence the observation of the fluorescence intensity may also be coupled to one another; for example, the vignetting may depend both on the location of the image sensor 23 or image sensors 61A, 61B and on the optical observation parameters of zoom, focus, and stop position. In this case, appropriately linked value tables or formulas are stored for the deviation factors.

In general, the correction method must be carried out separately for each pixel of the image sensor 23 or image sensors 61A, 61B, since some deviation factors depend on the location of the image sensor 23 or image sensors 61A, 61B (vignetting, for example). However, a majority of the deviation factors are independent of the location of the image sensor 23 or image sensors 61A, 61B (e.g., intensity setting of the light source), with the result that these represent global deviation factors for all locations on the image sensor 23 or image sensors 61A, 61B.

As a result of the above-described procedure, the reference object with 100 nM concentration of the fluorescent dye always has a corrected measurement value of 100 HE, and an actual object whose only deviation from the reference object is the concentration of the fluorescent dye of 33 nM always has a corrected measurement value of 33 HE, etc. Consequently, if all current parameter values of the parameters which influence the observation of the fluorescence intensity are known and if the respective arising deviation factors are stored correctly in the system, then the corrected signal depends only on the properties of the observation object 3 itself (e.g., optical properties, concentration of the fluorescent dye in the object, . . . ) and not on the settings of the surgical microscope 2 or the geometric position of the observation object 3 relative to the surgical microscope 2.

In a real system, it is not possible to determine and suitably correct all current parameter values of the parameter which influence the observation of the fluorescence intensity. However, it is possible to at least compensate the influences of as many of the parameters which influence the observation of the fluorescence intensity as possible, with the result that the corrected signal is (virtually) independent of at least the current parameter values of these parameters. In order nevertheless to obtain a reliable corrected signal, the user of the surgical microscope 2 should ensure that all parameters which influence the observation of the fluorescence intensity and which are not correctable by the system correspond to the reference conditions. For example, if the influence of the illumination intensity on the signal is not stored in correctable fashion in the system, then the user should ensure that the reference illumination intensity is set.

Naturally, the calibration can also be carried out if the simulation is only intended to determine, for each object region, the fluorescence intensity to be expected from the minimum concentration.

Fluorescent dyes such as PPIX slowly bleach upon excitation and successively lose fluorescence intensity. Therefore, the data processing unit 6 of a development of the optical observation system 100 depicted in FIG. 1 typically registers, for each object region 3A-H of the observation object 3, the duration for which the corresponding object region 3A-H has already been illuminated by the excitation wavelength. The fluorescence signal emanating from the respective object region 3A-H is then corrected in each case with the data processing unit 6 with a bleaching factor that is determined on the basis of the duration, or else an alert is displayed if the duration and intensity of the illumination with the excitation wavelength have exceeded a level considered compatible with the fluorescent dye. A tracking system and the determination of a depth map are typically provided in the case of a movement of the surgical microscope 2 relative to the observation object 3 in order to be able to assign the respective object regions 3A-H to the previous object regions 3A-H with the correct location in the new perspective. As it were, each object region 3A-H of the observation object 3 is provided with a counter which counts the amount of excitation light already radiated onto this point.

The present disclosure has been described in detail based on exemplary embodiments for explanatory purposes. However, a person skilled in the art recognizes that there can be deviations from the described exemplary embodiments within the scope of the disclosure. Therefore, the disclosure is not intended to be limited by the exemplary embodiments but rather only consists of the appended claims.

What is claimed is:

1. A method for creating at least one correction value for correcting fluorescence intensities in a fluorescence image obtained with an optical observation system, the optical observation system comprising an illumination system and an optical observation device in which the fluorescence image is formed by an image forming beam path, the method comprising:

determining a parameter value of at least one parameter of the optical observation system which influences an observation of fluorescence intensity; and generating the at least one correction value for correcting the fluorescence intensities in the fluorescence image based on the determined parameter value and an influence of the at least one parameter of the optical observation system, which influences the observation of the fluorescence intensity, on the fluorescence intensities in the fluorescence image, wherein the at least one parameter of the optical observation system, which influences the observation of fluorescence intensity, is a parameter of the illumination system, wherein at least one reference measurement with a reference concentration of a fluorescent dye is carried out with a reference parameter value for the at least one parameter which influences the observation of the fluorescence intensity to obtain a reference value for the fluorescence intensity at the reference concentration of the fluorescent dye, wherein a simulation of an expected fluorescence intensity is carried out, within the scope of which a change in the fluorescence intensity in comparison with the reference intensity is determined for a deviation of the parameter value of the at least one parameter which influences the observation of the fluorescence intensity from the reference parameter value, and wherein a compensation factor is determined, with which it is possible to compensate a change in the fluorescence intensity in a digital image which is caused by the deviation of the parameter value of the at least one parameter which influences the observation of the fluorescence intensity from the reference parameter value.

2. The method as claimed in claim 1, wherein at least one of the following parameters serves as the parameter of the illumination system:

a distance of an illumination system from an observation object, an orientation of the illumination system in relation to the observation object, an intensity of an illumination light source, a spectral intensity distribution of the illumination light source, a zoom setting of an illumination zoom, and a position of an illumination stop.

3. The method as claimed in claim 2, further comprising:

determining a current intensity of the illumination light source based on the value of a service life counter of the illumination light source and its nominally set intensity, with a degradation model for the illumination light source.

4. The method as claimed in claim 3, further comprising:

providing a degradation model which, in addition to the change in the overall intensity of the illumination light source, also takes account of the shifts in the spectral intensity distribution of the illumination radiation that occur over time.

5. The method as claimed in claim 3, wherein the current intensity of the illumination light source is determined based on a calibration target and the intensity of the reflected illumination light which is detected when the calibration target is used with the optical observation device.

6. The method as claimed in claim 3, wherein the current intensity of the illumination light source is determined with an intensity sensor.

7. The method as claimed in claim 2, further comprising:

calculating a fluorescence radiation emitted by at least one surface region of the observation object, with the spectral intensity distribution of the illumination light source being weighted in the calculation by the effective spectral excitation curve of the fluorescence.

8. The method as claimed in claim 1, wherein the parameter value is at least one of:

a distance of the optical observation device from an observation object, an orientation of the optical observation device in relation to the observation object, a zoom setting of the optical observation device, a front focal distance of the optical observation device, a stop setting of the optical observation device, a gain of an image sensor used in the optical observation device, an exposure duration of an image sensor used in the optical observation device, and nonlinearities of an image sensor used in the optical observation device.

9. The method as claimed in claim 1, wherein the optical observation device is at least one of:

a surgical microscope, an endoscope, or a camera.

10. A computer-implemented method for creating at least one correction value for correcting fluorescence intensities in a fluorescence image obtained with an optical observation system, the optical observation system comprising an illumination system and an optical observation device in which the fluorescence image is formed by an image forming beam path, the method comprising:

receiving or retrieving a parameter value of at least one parameter of the optical observation system which influences an observation of fluorescence intensity; and generating the at least one correction value for correcting the fluorescence intensities in the fluorescence image based on the received or retrieved parameter value and an influence of the at least one parameter of the optical observation system, which influences the observation of the fluorescence intensity, on the fluorescence intensities in the fluorescence image, wherein the at least one parameter of the optical observation system, which influences the observation of the fluorescence intensity, is a parameter of the illumination system, wherein at least one reference measurement with a reference concentration of a fluorescent dye is carried out with a reference parameter value for the at least one parameter which influences the observation of the fluorescence intensity to obtain a reference value for the fluorescence intensity at the reference concentration of the fluorescent dye, wherein a simulation of an expected fluorescence intensity is carried out, within the scope of which a change in the fluorescence intensity in comparison with the reference intensity is determined for a deviation of the parameter value of the at least one parameter which influences the observation of the fluorescence intensity from the reference parameter value, and wherein a compensation factor is determined, with which it is possible to compensate a change in the fluorescence intensity in a digital image which is caused by the deviation of the parameter value of the at least one parameter which influences the observation of the fluorescence intensity from the reference parameter value.

11. The computer-implemented method as claimed in claim 10, wherein the optical observation device is at least one of:

a surgical microscope, an endoscope, or a camera.

12. A non-transitory computer-readable storage medium to store a computer program for creating at least one correction value for correcting fluorescence intensities in a fluorescence image obtained with an optical observation system, the optical observation system comprising an illumination system and an optical observation device in which the fluorescence image is formed by an image forming beam path, the computer program comprising instructions which, when executed on a computer, cause the computer to:

receive or retrieve a parameter value of at least one parameter of the optical observation system which influences an observation of fluorescence intensity; and generate the at least one correction value for correcting the fluorescence intensities in the fluorescence image based on the received or retrieved parameter value and an influence of the at least one parameter of the optical observation system, which influences the observation of the fluorescence intensity, on the fluorescence intensities in the fluorescence image, wherein the at least one parameter of the optical observation system, which influences the observation of the fluorescence intensity, is a parameter of the illumination system, wherein at least one reference measurement with a reference concentration of a fluorescent dye is carried out with a reference parameter value for the at least one parameter which influences the observation of the fluorescence intensity to obtain a reference value for the fluorescence intensity at the reference concentration of the fluorescent dye, wherein a simulation of an expected fluorescence intensity is carried out, within the scope of which a change in the fluorescence intensity in comparison with the reference intensity is determined for a deviation of the parameter value of the at least one parameter which influences the observation of the fluorescence intensity from the reference parameter value, and wherein a compensation factor is determined, with which it is possible to compensate a change in the fluorescence intensity in a digital image which is caused by the deviation of the parameter value of the at least one parameter which influences the observation of the fluorescence intensity from the reference parameter value.

13. The non-transitory computer-readable storage medium as claimed in claim 11, wherein the optical observation device is at least one of:

a surgical microscope, an endoscope, or a camera.

14. A data processing unit for creating at least one correction value for correcting fluorescence intensities in a fluorescence image obtained with an optical observation system, the optical observation system comprising an illumination system and an optical observation device in which the fluorescence image is formed by an image forming beam path, the data processing unit comprising:

a memory in which a computer program is stored; and a processor configured to:

receive or retrieve a parameter value of at least one parameter of the optical observation system, which influences an observation of fluorescence intensity;

generate the at least one correction value for correcting the fluorescence intensities in the fluorescence image based on the received or retrieved parameter value and an influence of the at least one parameter of the observation system, which influences the observation of the fluorescence intensity, on the fluorescence intensities in the fluorescence image; and output the at least one correction value, wherein the at least one parameter of the optical observation system, which influences the observation of the fluorescence intensity, is a parameter of the illumination system, wherein at least one reference measurement with a reference concentration of a fluorescent dye is carried out with a reference parameter value for the at least one parameter which influences the observation of the fluorescence intensity to obtain a reference value for the fluorescence intensity at the reference concentration of the fluorescent dye, wherein a simulation of an expected fluorescence intensity is carried out, within the scope of which a change in the fluorescence intensity in comparison with the reference intensity is determined for a deviation of the parameter value of the at least one parameter which influences the observation of the fluorescence intensity from the reference parameter value, and wherein a compensation factor is determined, with which it is possible to compensate a change in the fluorescence intensity in a digital image which is caused by the deviation of the parameter value of the at least one parameter which influences the observation of the fluorescence intensity from the reference parameter value.

15. The data processing unit as claimed in claim 14, wherein the optical observation device is at least one of:

a surgical microscope, an endoscope, or a camera.

16. An optical observation system, comprising:

an illumination system;

an optical observation device; and the data processing unit as claimed in claim 14.

17. The optical observation system as claimed in claim 16, further comprising an intensity sensor, wherein the processor is further configured to at least one of:

register the service life of an illumination source to date;

determine a distance of the illumination system from an observation object and/or an orientation of the illumination system in relation to the observation object;

determine a zoom position of an illumination zoom; and determine a position of an illumination stop.

18. The optical observation system as claimed in claim 16, further comprising:

a controller configured to automatically set at least one parameter value of the optical observation system.

* * * * *